United States Patent
Fridman et al.

(10) Patent No.: US 9,339,783 B2
(45) Date of Patent: May 17, 2016

(54) TUBULAR FLOATING ELECTRODE DIELECTRIC BARRIER DISCHARGE FOR APPLICATIONS IN STERILIZATION AND TISSUE BONDING

(71) Applicant: DREXEL UNIVERSITY, Philadelphia, PA (US)

(72) Inventors: Gregory Fridman, Philadelphia, PA (US); Alexander Fridman, Philadelphia, PA (US); Alexander F. Gutsol, San Ramon, CA (US); Gennady Friedman, Richboro, PA (US); David Staack, College Station, TX (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/322,113

(22) Filed: Jul. 2, 2014

(65) Prior Publication Data
US 2014/0311891 A1    Oct. 23, 2014

Related U.S. Application Data

(62) Division of application No. 13/256,301, filed as application No. PCT/US2010/027376 on Mar. 16, 2010, now abandoned.

(60) Provisional application No. 61/160,596, filed on Mar. 16, 2009.

(51) Int. Cl.
*H05F 3/00*     (2006.01)
*B01J 19/08*    (2006.01)
(Continued)

(52) U.S. Cl.
CPC ............. *B01J 19/087* (2013.01); *A61L 2/0011* (2013.01); *A61L 2/14* (2013.01); *H05H 1/2406* (2013.01); *H05H 2001/245* (2013.01); *H05H 2001/2456* (2013.01); *H05H 2245/122* (2013.01)

(58) Field of Classification Search
CPC ...... A61L 2/00211; A61L 2/14; B01J 19/087; H05H 1/24; H05H 1/2406; H05H 2001/245; H05H 2001/2456; H05H 2245/122; H01T 23/00; A61B 18/042; A61N 1/40; B05D 1/62
See application file for complete search history.

(56) References Cited

U.S. PATENT DOCUMENTS

| 2004/0050684 A1 | 3/2004 | Babko-Malyi et al. |
| 2005/0063879 A1 | 3/2005 | Tsuji |

(Continued)

OTHER PUBLICATIONS

Fridman et al., "Applied Plasma Medicine", Plasma Processes and Polymers, Review, Apr. 2008, 5(6), 503-533.
(Continued)

*Primary Examiner* — Xiuyu Tai
(74) *Attorney, Agent, or Firm* — Baker & Hostetler LLP

(57) ABSTRACT

Disclosed is a device and method for contacting a biological substrate. A non-thermal plasma device delivers a non-thermal plasma discharge using a dielectric conduit, an igniter electrode and a RF electrode. The dielectric conduit fluidicly communicates a gas therethrough and an igniter electrode ionizes at least a portion of the gas. The RF electrode, disposed circumferentially proximate to the exterior of the dielectric conduit, generates non-thermal plasma from the ionized gas. The non-thermal plasma is discharged from the dielectric conduit and contacts a biological substrate. The non-thermal plasma discharge may be suitable for tissue bonding and sterilization applications.

18 Claims, 7 Drawing Sheets

(51) Int. Cl.
*A61L 2/00* (2006.01)
*A61L 2/14* (2006.01)
*H05H 1/24* (2006.01)

(56) References Cited

U.S. PATENT DOCUMENTS

| 2005/0205410 | A1 | 9/2005 | Babko-Malyi |
| 2005/0211685 | A1 | 9/2005 | Blankenship |
| 2007/0029500 | A1 | 2/2007 | Coulombe et al. |
| 2007/0286954 | A1 | 12/2007 | Tang et al. |
| 2011/0042560 | A1 | 2/2011 | Ouyang et al. |

OTHER PUBLICATIONS

Hong et al., "Modeling High-Pressure Microplasmas: Comparison of Fluid Modeling and Particle-in-Cell Monte Carlo Collision Modeling", Plasma Processes and Polymers, Full Paper, Aug. 15, 2008, 5(6), 583-592.

Laroussi et al., "Plasma Medicine", Plasma Processes and Polymers, Apr. 2008, 5(6), 501-502.

Moreau et al., "Non-Thermal Plasma Technologies: New Tools for Bio-Decontamination", Biotechnologies Advances, Apr. 7, 2008, 25, 610-617.

Park et al., "Global Model of He/$O_2$ and Ar/$O_2$ Atmospheric Pressure Glow Discharges", Plasma Processes and Polymers, Apr. 2008, 5(6), 569-576.

Perez-Martinez et al., "Power Supply for Plasma Torches Based on a Class-E Amplifier Configuration", Plasma Processes and Polymers, Full Paper, Apr. 2008, 5(6), 593-598.

Pointu et al., "Nitrogen Atmospheric Pressure Post Discharges for Surface Biological Decontamination inside Small Diameter Tubes", Plasma Processes and Polymers, Full Paper, Apr. 2008, 5(6), 559-568.

Sardella et al., "Nano-Structured Cell-Adhesive and Cell-Repulsive Plasma-Deposited Coatings: Chemical and Topographical Effects on Keratinocyte Adhesion", Plasma Processes and Polymers, Full Paper, Apr. 2008, 5(6), 540-551.

Sato et al., "Generation and Transportation Mechanisms of Chemically Active Species by Dielectric Barrier Discharge in a Tube for Catheter Sterilization", Plasma Processes and Polymers, Full Paper, Apr. 2008, 5(6), 606-614.

Shimizu et al., "Characterization of Microwave Plasma Torch for Decontamination", Plasma Processes and Polymers, Full Paper, Apr. 2008, 5(6), 577-582.

Stoffels et al., "Delayed Effects of Cold Atmospheric Plasma on Vascular Cells", Plasma Processes and Polymers, Full Paper, Apr. 28, 2010, 5(6), 599-605.

Tang et al., "Sublethal and Killing Effects of Atmospheric-Pressure, Nonthermal Plasma on Eukaryotic Microalgae in Aqueous Media", Plasma Processes and Polymers, Full Paper, Apr. 2008, 5(6), 552-558.

PCT Application No. PCT/US2010/27376 : International Search Report and Written Opinion of the International Searching Authority, Apr. 28, 2010, 9 pages.

von Woedtke et al., "Plasma Sterilization: What are the Conditions to Meet this Claim?", Plasma Processes and Polymers, Full Paper, Apr. 15, 2008, 5(6), 534-539.

Yasuda et al., "States of Biological Components in Bacteria and Bacteriophages during Inactivation by Atmospheric Dielectric Barrier Discharges", Plasma Processes and Polymers, Full Paper, 2008, 5(6), 615-612.

TUBULAR FLOATING ELECTRODE DIELECTRIC BARRIER DISCHARGE FOR APPLICATIONS IN STERILIZATION AND TISSUE BONDING

CROSS-REFERENCE TO RELATED APPLICATION

This application is a divisional of U.S. patent application Ser. No. 13/256,301, filed Dec. 8, 2011, which is a National Stage Entry of International Application No. PCT/US2010/027376, filed Mar. 16, 2010, which claims the benefit of U.S. Provisional Patent Application, Ser. No. 61/160,596, filed Mar. 16, 2009, the contents of which are hereby incorporated by reference in their entireties.

TECHNICAL FIELD

The invention relates to the field of generating non-thermal plasmas. The invention also relates to sterilization and tissue bonding.

BACKGROUND

Plasmas, referred to as the "fourth state of matter," are ionized gases having at least one electron that is not bound to an atom or molecule. In recent years, plasmas have become of significant interest to researchers in the fields such as organic and polymer chemistry, fuel conversion, hydrogen production, environmental chemistry, biology, and medicine, among others. This is, in part, because plasmas offer several advantages over traditional chemical processes. For example, plasmas can generate much higher temperatures and energy densities than conventional chemical technologies; plasmas are able to produce very high concentrations of energetic and chemically active species; and plasma systems can operate far from thermodynamic equilibrium, providing extremely high concentrations of chemically active species while having a bulk temperature as low as room temperature. Many details concerning the generation and applications of plasmas are described in PLASMA CHEMISTRY (2008), by Friedman.

Plasmas are generated by ionizing gases using any of the variety of ionization sources. Depending upon the ionization source and the extent of ionization, plasmas may be characterized as either thermal or non-thermal. Thermal and non-thermal plasmas can also be characterized by the temperature of their components. Thermal plasmas are in a state of thermal equilibrium, that is, the temperature of the free electrons, ions, and heavy neutral atoms are approximately the same. Non-thermal plasmas, or cold plasmas, are far from a state of thermal equilibrium; the temperature of the free electrons is much greater than the temperature of the ions and heavy neutral atoms within the plasma.

The initial generation of free electrons may vary depending upon the ionization source. With respect to both thermal and non-thermal ionization sources, electrons may be generated at the surface of the cathode due to a potential applied across the electrode. In addition, thermal plasma ionization sources may also generate electrons at the surface of a cathode as a result of the high temperature of the cathode (thermionic emissions) or high electric fields near the surface of the cathode (field emissions).

The energy from these free electrons may be transferred to additional plasma components, providing energy for additional ionization, excitation, dissociation, etc. With respect to non-thermal plasmas, the ionization process typically occurs by direct ionization through electron impact. Direct ionization occurs when an electron of high energy interacts with a valence electron of a neutral atom or molecule. If the energy of the electron is greater than the ionization potential of the valence electron, the valence electron escapes the electron cloud of the atom or molecule and becomes a free electron according to:

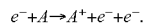

$$e^-+A \rightarrow A^+ +e^- +e^-.$$

As the charge of the ion increases, the energy required to remove an additional electron also increases. Thus, the energy required to remove an additional electron from $A^+$ is greater than the energy required to remove the first electron from A to form $A^+$. A benefit of non-thermal plasmas is that because complete ionization does not occur, the power to the ionization source can be adjusted to increase or decrease ionization. This ability to adjust the ionization of the gas provides for a user to "tune" the plasma to their specific needs.

Although thermal plasmas are capable of delivering extremely high powers, they have several drawbacks. For example, thermal plasmas do not allow for adjusting the amount of ionization, they operate at extremely high temperatures, they lack efficiency, and may have electrode erosion problems.

Non-thermal plasma ionization sources have alleviated some of the above mentioned problems. Exemplary ionization sources for non-thermal plasmas include glow discharges, floating electrode dielectric barrier discharges (FE-DBD), and gilding arc discharges among others. In contrast to thermal plasmas, non-thermal plasmas provide for high selectivity, high energy efficiencies, and low operating temperatures. In many non-thermal plasma systems, electron temperatures are at about 10,000 K while the bulk gas temperature may be as cool as room temperature.

Dielectric barrier discharge (DBD) may be performed using an alternating current at a frequency of from about 0.5 kHz to about 500 kHz between a high voltage electrode and a ground electrode. In addition, one or more dielectric barriers are placed between the electrodes. DBDs have been employed for over a century and have been used for the generation of ozone in the purification of water, polymer treatment (to promote wettability, printability, adhesion), and for pollution control. DBDs prevent spark formation by limiting current between the electrodes.

Several materials can be utilized for the dielectric barrier. These include glass, quartz, and ceramics, among others. The clearance between the discharge gaps is typically between about 0.1 mm and several centimeters. The required voltage applied to the high voltage electrode varies depending upon the pressure and the clearance between discharge gaps. For a DBD at atmospheric pressure and a few millimeters between the gaps, the voltage required to generate a plasma is about 10 kV.

In certain embodiments, the ground electrode of the DBD may be an external conductive object, such as a human body. This is known as floating-electrode DBD (FE-DBD). FE-DBD has recently been utilized in medical applications.

SUMMARY

The present invention provides for methods and non-thermal plasma devices for contacting a biological substrate. The present invention also provides for methods and non-thermal plasma devices for utilizing the non-thermal plasma for tissue bonding and sterilization applications.

The present invention provides non-thermal plasma devices for contacting a biological substrate comprising: a dielectric conduit capable of fluidicly communicating a gas, plasma, or both, therethrough, the dielectric conduit characterized as comprising an upstream end and a downstream end, the upstream end capable of receiving gas from a gas source, and the downstream end capable of transmitting non-thermal plasma therefrom; an igniter electrode disposed within the upstream portion of the dielectric conduit, the igniter electrode capable of being energized to give rise to non ionized gas proximately located to the igniter electrode; and a RF electrode disposed downstream relative to the gas source, the RF electrode capable of generating non-thermal plasma from the ionized gas.

Additionally, the non-thermal plasma device may further comprise a gas source capable of supplying gas to the upstream end of the dielectric conduit and a power supply capable of supply RF power to the RF electrode.

Another aspect of the present invention relates to methods for contacting a biological substrate with non-thermal plasma comprising: fluidicly communicating a gas through a dielectric conduit characterized as comprising an upstream end and a downstream end, the upstream end capable of receiving gas from a gas source, and the downstream end capable of transmitting non-thermal plasma therefrom; ionizing at least a portion of the gas using an igniter electrode disposed within the upstream portion of the dielectric conduit, the igniter electrode capable of being energized to give rise to ionized gas proximately located to the igniter electrode; generating non-thermal plasma from ionized gas using an RF electrode disposed circumferentially proximate to the exterior of the dielectric conduit, the RF electrode disposed downstream relative to the gas source; and contacting the biological substrate with non-thermal plasma discharge. Additionally, the method may further comprise placing the biological substrate at a first distance from the downstream opening of the dielectric conduit, and placing the biological substrate at a second distance from the downstream opening of the dielectric conduit, wherein the second distance is closer to the downstream opening of the dielectric conduit in comparison to the first distance.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Other features of the subject matter are described below.

BRIEF DESCRIPTION OF THE DRAWINGS

The summary, as well as the following detailed description, is further understood when read in conjunction with the appended drawings. For the purpose of illustrating the subject matter, there are shown in the drawings exemplary embodiments of the subject matter; however, the presently disclosed subject matter is not limited to the specific methods, compositions, and devices disclosed. In addition, the drawings are not necessarily drawn to scale. In the drawings.

DETAILED DESCRIPTION OF ILLUSTRATIVE EMBODIMENTS

The present subject matter may be understood more readily by references to the following detailed description taken in connection with the accompanying figures and examples, which form a part of this disclosure. It is to be understood that this invention is not limited to the specific device, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Disclosed are non-thermal plasma devices for contacting a biological substrate, and methods for contacting a biological substrate with the non-thermal plasma. The device and method may be easily employed by either a human operator, or a remotely controlled machine.

Figure 1:
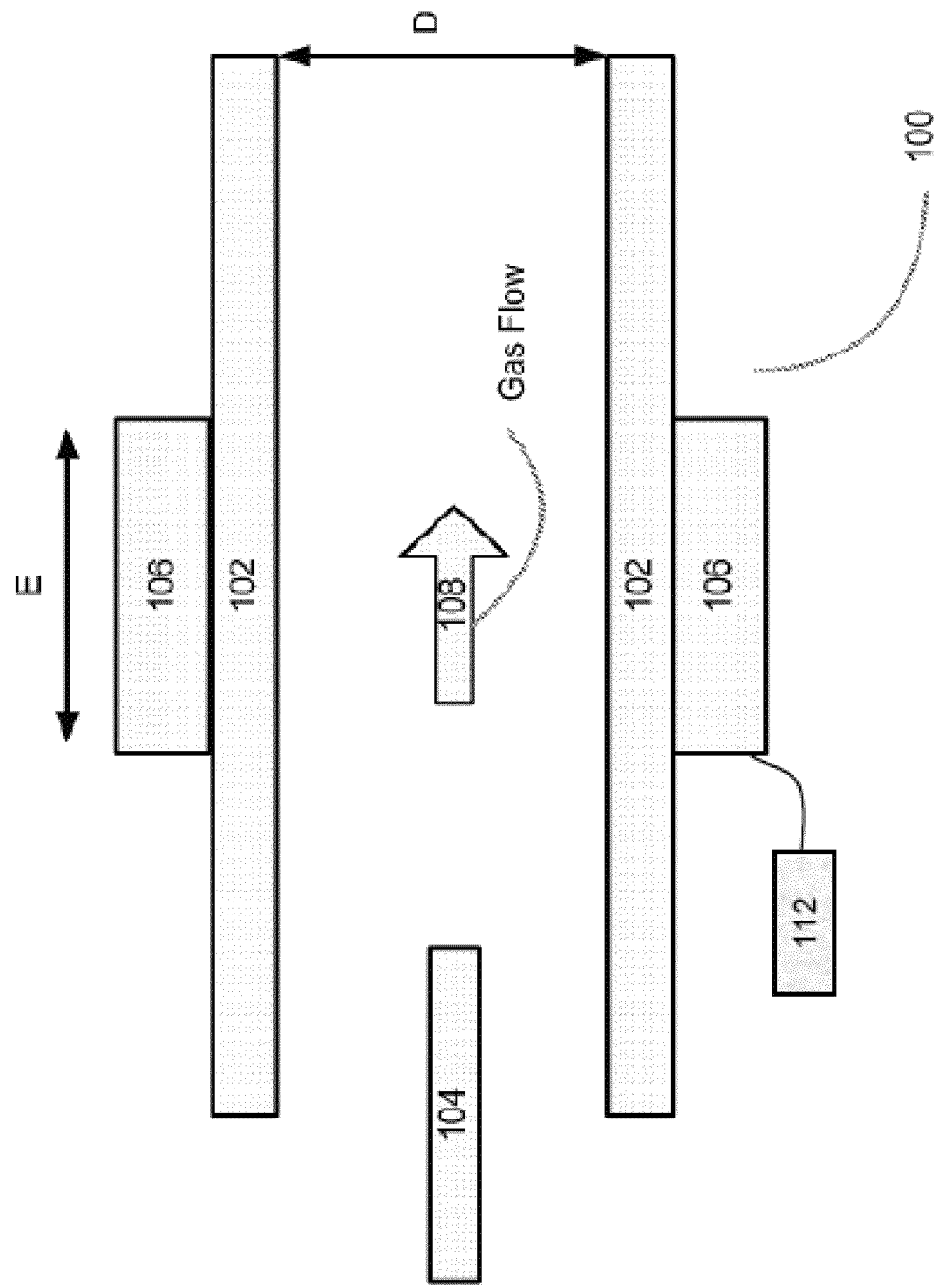
FIG. 1 is a block diagram showing a cross section of a non-thermal plasma device for contacting a biological substrate.

FIG. 1 is a block diagram showing a cross section of a non-thermal plasma device for contacting a biological substrate. The non-thermal plasma device may be a floating electrode dielectric barrier discharge (FE-DBD). For the purposes of this disclosure, a "substrate" is any soft tissue, biological tissue, metal, or plastic. For example, a substrate may be skin or an internal organ. Additionally, a "jet," for the purposes of this disclosure, is the non-thermal plasma discharge transferred out of a dielectric conduit.

In FIG. 1, device 100 comprises a dielectric conduit 102, an igniter electrode 104, and a RF electrode 106. The dielectric conduit 102 is capable of fluidicly communicating a gas, plasma, or both, therethrough. Additionally, the dielectric conduit 102 may comprise an upstream end and a downstream end. The upstream end is capable of receiving gas from a gas source, and the downstream end is capable of transferring non-thermal plasma out of the dielectric conduit 102. As illustrated by direction arrow 108, gas flows from the upstream end to the downstream end. Dielectric conduit 102 may comprise dielectric material, typically insulator material, such as glass, quartz, plastic, ceramic, porcelain, or any combination thereof. Additionally, dielectric conduit 102 may also vary in size, and its diameter D, as shown in FIG. 1, can be in the range of about 0.2 mm to about 1 cm. The varying diameter D of dielectric conduit 102 may impact the width of the jet, which may increase with an increasing diameter D of dielectric conduit 102. Additionally, with a large diameter D dielectric conduit 102, the non-thermal plasma may propagate along the interior surface of dielectric conduit 102. As the current of the gas flow is increased, the non-thermal plasma discharge can cover a greater interior surface area of the dielectric conduit 102. In a small diameter D dielectric conduit 102, the non-thermal plasma discharge may concentrate proximate to the centerline. The centerline being the center of the lumen, or space within dielectric conduit 102. Additionally, a dielectric conduit 102 with an intermediate diameter D can exhibit both surface and centerline plasmas.

The igniter electrode 104 is disposed within the upstream portion of the dielectric conduit and is capable of being energized to give rise to ionized gas that is proximately located to igniter electrode 104. The igniter electrode 104 may be proximate to the center of the lumen, which is the space within dielectric conduit 102. Additionally, the igniter electrode 104 may also be located anywhere within the lumen of dielectric conduit 102. Igniter electrode 104 may comprise a metal or any combination of metals, such as, but not limited to, tungsten, copper, gold, silver, iron, titanium, platinum, aluminum, or any combination thereof. Furthermore, igniter electrode 104 may be any particular shape, such as a cylinder, cube, rectangular prism, or pyramid. Optionally, suitable igniter electrode 104 may be a wire. In addition, igniter electrode 104 may be either floating or grounded relative to device 100. Suitable igniter electrode 104 need not be connected to ground or anything else; it can be floating.

As previously mentioned, FIG. 1 depicts a cross section of device 100. In FIG. 1, RF electrode 106 may be disposed circumferentially proximate to the exterior of dielectric conduit 102. Additionally, RF electrode 106 may be disposed downstream relative to the gas source and capable of generating non-thermal plasma from ionized gas. Suitable RF electrode 106 may be circumferentially directly adjacent to the exterior of dielectric conduit 102. RF electrode 106 may also be directly adjacent or proximate to the exterior of dielectric conduit 102. Additionally, RF electrode 106 may comprise either a single electrode or patches of electrodes. RF electrode 106 may also be connected to a power supply 112 which is configured to supply high voltage RF power to RF electrode 106. Floating electrode dielectric barrier discharge (FEDBD) may be performed using an alternating current at a frequency in the range of about 0.5 kHz to about 500 kHz between a high voltage electrode and a ground electrode. It should be noted that in certain configurations, a single pulse may be used. Therefore, the present subject matter may be preferably used in applications ranging from a single pulse to about 500 kHz. Additionally, the power output of the power supply may be in a range of about 0.5 Watt/cm$^2$ to about 2 Watt/cm$^2$. Suitable RF electrode 106 may comprise of any conducting material, whether liquid or metal, such as aluminum foil, stainless steel, stainless steel mesh, copper, silver, or any combination thereof.

Furthermore, RF electrode 106 may vary in length L, as illustrated in FIG. 1. Length L may be in the range of about 1 mm to about 20 cm. Length L may impact what type of discharge can be created. For example, but not intending to limit, for a helium gas with a short RF electrode 106, length L in the range of about 1 mm to about 5 cm, the discharge appears to be the same with plasma visible both below RF electrode 106 and in a jet both upstream and downstream of RF electrode 106. Additionally, RF electrode 106 with a length L of about 20 cm only fills dielectric conduit with plasma for about 5 cm penetrations both upstream and downstream of RF electrode 106 when used with helium gas. RF electrode 106 with a length 107 of 10 cm does not have an apparent plasma within dielectric conduit 102 when used with a helium gas.

Figure 2:
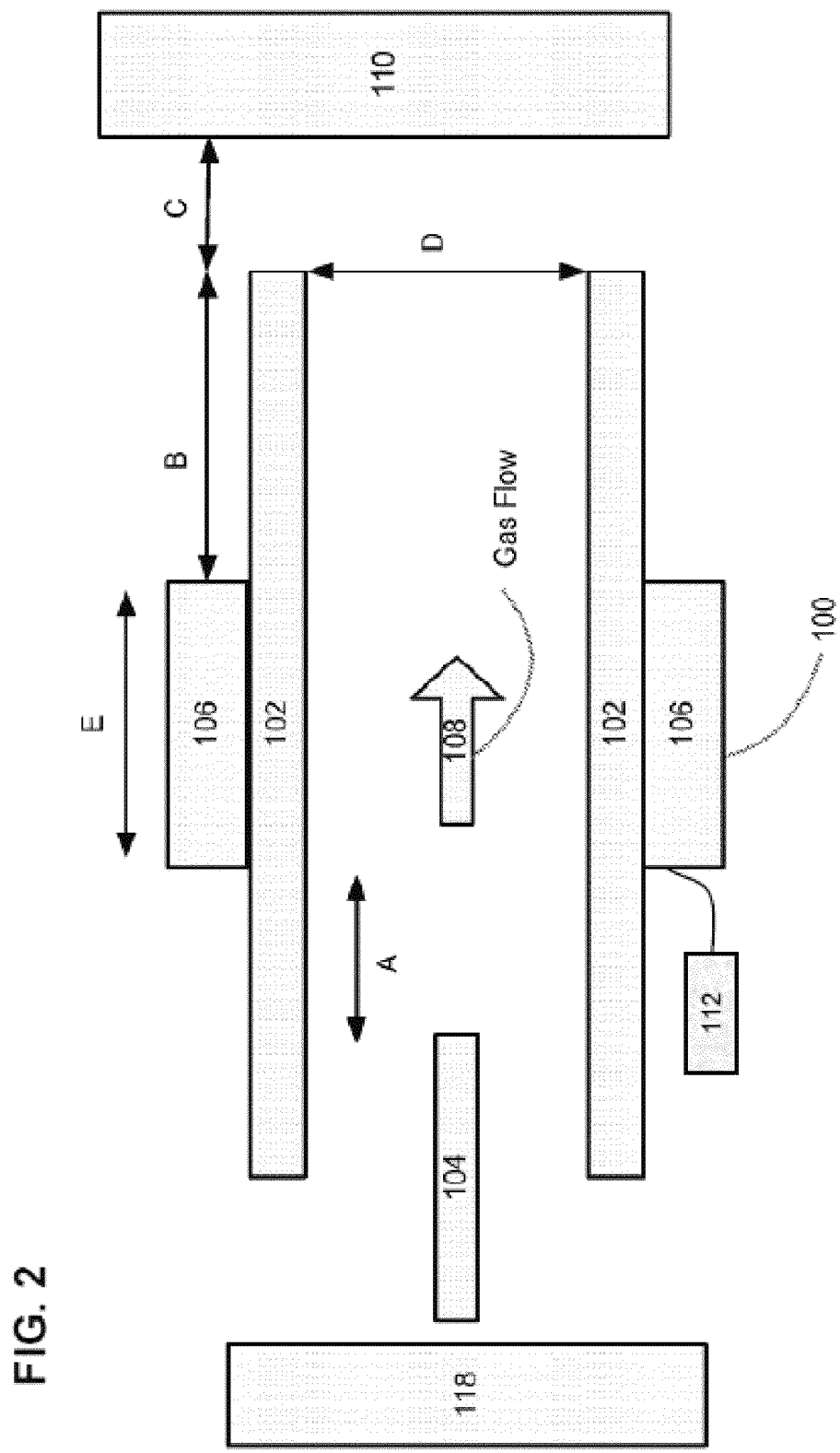
FIG. 2 is a block diagram showing a cross section of a non-thermal plasma device for contacting a biological substrate.

FIG. 2 is a block diagram showing a cross section of a non-thermal plasma device for contacting a biological substrate. In addition to device 100, FIG. 2 further depicts substrate 110, gas source 118, and distances B, C, and A. Substrate 100 may be located downstream from the downstream opening of dielectric conduit 102. Additionally, substrate 100 may comprise biological soft tissue, plastic, or metal. Suitable substrate 110 may also serve as an electrode to device 100.

In FIG. 2, gas source 118 supplies gas to the upstream end of dielectric conduit 102. As previously discussed, the gas flows in the direction of arrow 108. Gas provided by gas source 118 may comprise any gas or combination of gases, such as helium, argon, nitrogen, air, or any combination thereof.

FIG. 2 further depicts distances B, C, and A. Distance B is the distance between RF electrode 106 and downstream opening of dielectric conduit 102. Distance C is the distance between the downstream opening of dielectric conduit 102 and substrate 110. Additionally, distance A is the distance between igniter electrode 104 and RF electrode 106. Distance A may also be negative when igniter electrode 104 is positioned inside RF electrode.

Figure 3:
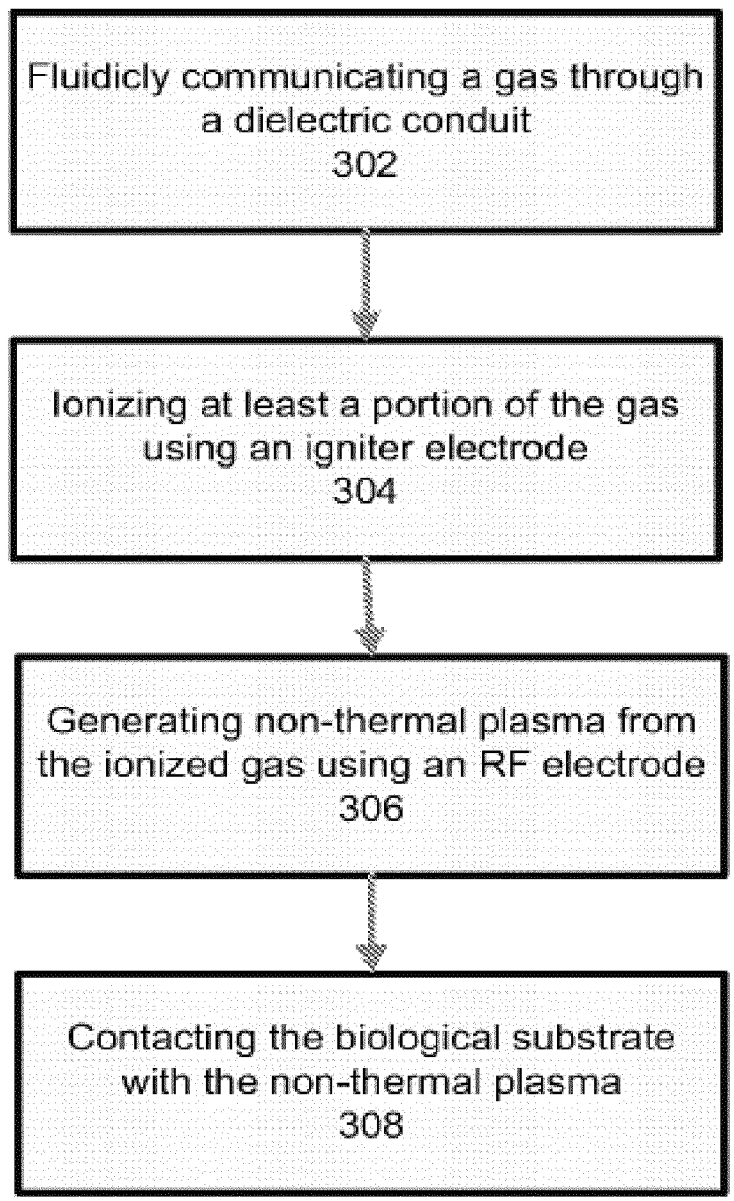
FIG. 3 is a flow chart of a non-limiting, exemplary method of contacting a biological substrate with non-thermal plasma.

FIG. 3 is a flow chart of a non-limiting, exemplary method of contacting biological substrate with non-thermal plasma. At step 302, dielectric conduit 102 fluidicly communicates gas through. Gas can be supplied to the upstream end of dielectric conduit 102 via gas source 118. Additionally, the gas may pass through the lumen of dielectric conduit 102 and in the direction of arrow 108, moving upstream to downstream.

At step 304, igniter electrode 104 ionizes at least a portion of the gas proximately located. As previously mentioned, igniter electrode 104 may be located proximate to the center of the lumen of dielectric conduit 102. Without being bound by any limitation or theory of operation of the invention, it is believed that the presence of igniter electrode 104 modifies the electric field within dielectric conduit 102, creating a strong electric field near igniter electrode 104 and also near the corner of the RF electrode 106, thus, allowing ionization of at least a portion of the gas proximately located to igniter electrode 104. As the gas passes within proximately to the igniter electrode 104, the electrons may receive energy from the electric field to escape from the electric potential barrier that originally confined it, thereby allowing the bond between electron and atom to break and freeing the electrons to move to an excited state. At step 306, non-thermal plasma is generated from the ionized gas using RF electrode 106. Without being bound by any limitation or theory of operation of the invention, it is believed that as the free moving electrons continuously alternate between an excited state and a ground state, they give off energy in the form of light and heat and generate plasma.

Additionally, without being bound by any limitation or theory of operation of the invention, it is believed that distance A between igniter electrode 104 and RF electrode 106 may be altered in order to generate a stronger electric field within the dielectric conduit 102. As distance A is increased positively, the electric field may become weaker. Conversely, as distance A becomes more negative, the electric field may become stronger.

At step 308, non-thermal plasma is discharged from the downstream end of dielectric conduit 102. The non-thermal plasma discharge may be in the form of a jet and may contact substrate 110. At step 308, there may be either no substrate 110, or substrate 110 may be far away, or substrate 100 may be a dielectric with a small capacitance. In that case, the non-thermal plasma discharge may operate in a detached mode. In a detached mode, the emanating jet is dim, largely unperturbed and operating only as an afterglow. Additionally, in a detached mode, the jet can exit from dielectric conduit 102 and may be in the shape of a uniformly luminous cone. Furthermore, the detached mode may be ineffective for sterilization purposes and tissue bonding applications.

Additionally, at step 308, substrate 110 may also be at a first distance away from the downstream opening of the dielectric conduit 102. At the first distance, the non-thermal plasma discharge may impinge the surface of substrate 110, transferring to substrate 110, thus, operating in a transferring mode. For example, but not intending to limit, for a dielectric conduit 102 with a 6 mm diameter, it is believed that the non-thermal plasma discharge may operate in a transferring mode when distance B and distance C add up to equal a distance in the range of about 1 cm and about 7 cm. Additionally, the transferring mode may occur with a capacitive or grounded substrate 110. In the transferring mode, the jet may become more intense and can reach out from the side of the jet toward the substrate 110, in a cloud shape. Furthermore, without being bound by any limitation or theory of operation of the invention, it is believed that the transferring mode can be effective for tissue bonding and sterilization. Exposing substrate 110 to the non-thermal plasma discharge, in the transferring mode, for times ranging from about 3 seconds to about 2 minutes resulted in the non-thermal plasma discharge killing bacteria. The longer the exposure and the more intense the plasma discharge, the more effective the plasma discharge may be for sterilization purposes. Additionally, in the transferring mode, the non-thermal plasma discharge can also be effective for tissue bonding applications. The device may be able to perform three types of tissue bonding: 1.) thermal coagulative bonding, 2.) chemical denaturing bonding, or a chemical bonding of the tissue, and 3.) blood coagulation bonding, a natural process by which blood coagulate and stiffens. Thus, the non-thermal plasma discharge may also be effective for tissue bonding while simultaneously sterilizing the treated area.

Figure 4:
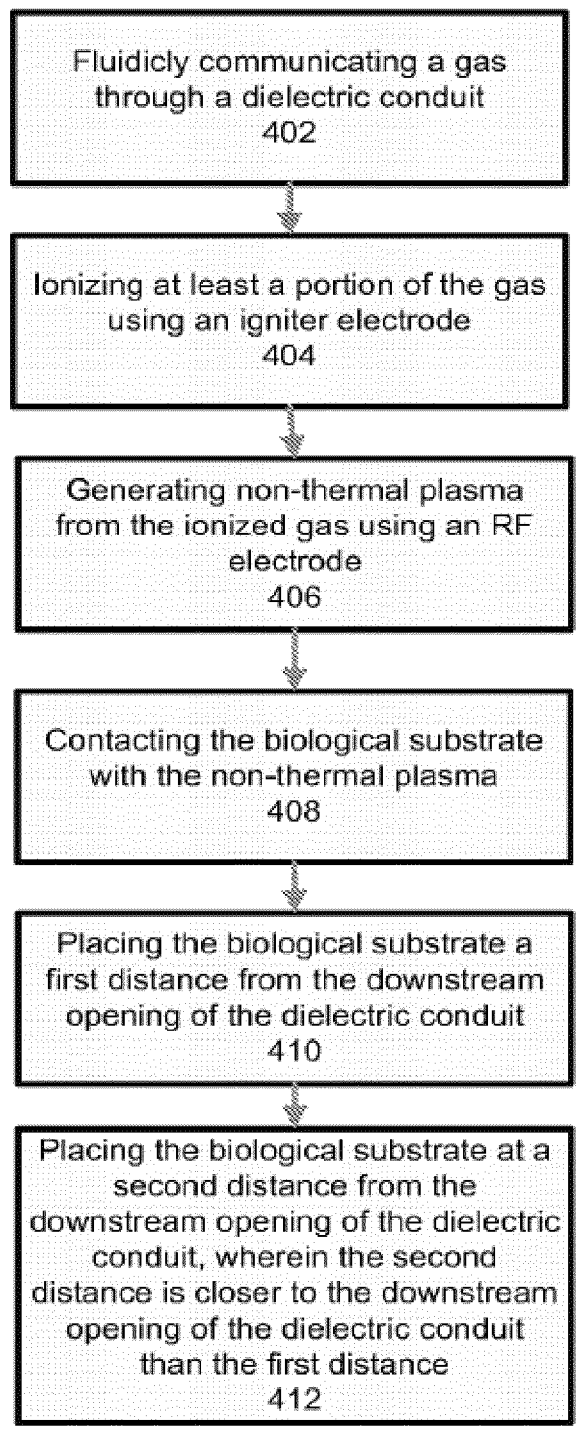
FIG. 4 is a flow chart of a non-limiting, exemplary alternative method of contacting a biological substrate with non-thermal plasma.

FIG. 4 is a flow chart of a non-limiting, exemplary alternative method of contacting biological substrate with non-thermal plasma in a transferring and attached mode.

As discussed above with respect to FIG. 3, at step 402, the dielectric conduit fluidicly communicates a gas through. At step 404, the igniter electrode 104 ionizes at least a portion of the gas, and the RF electrode 106 generates non-thermal plasma from the ionized gas at step 406. At step 408, the non-thermal plasma discharge contacts substrate 110. At step 410, the biological substrate is placed at a first distance from the downstream opening of the dielectric conduit 102. Step 410 illustrates the non-thermal plasma discharge operating in a transferring mode as previously discussed.

At step 412, substrate 110 is placed at a second distance from the downstream opening of the dielectric conduit 102, wherein the second distance is closer to the downstream opening of the dielectric conduit 102 than the first distance. As substrate 110 is moved from the first distance to the second distance a more focused, intense micro-column may impinge on the substrate 110 and may be transferred to substrate 110 in an attached mode. For example, using dielectric conduit 102 with a diameter of 6 mm, as previously described where the non-thermal discharge operates in the transferring mode when distances B and C total a distance in the range of about 1 cm and about 7 cm, it is believed that the attached mode may occur when distances B and C total less than about 1 cm. The attached mode may be most effective for sterilization purposes. Without being bound by any limitation or theory of operation of the invention, it is believed that the attached mode may create the strongest bonds between biological soft tissue in comparison to the detached and transferring modes. Additionally, the non-thermal plasma discharge of the attached mode may cause browning and blackening of the soft tissue along with severe drying.

This method for contacting biological substrates with non-thermal plasma has many applications in the medical field. For example, but not intending to limit, hospitals may utilize this treatment for simultaneously closing wounds and sterilizing the surrounding area. Additionally, because of the relatively small size of the non-thermal plasma device, it may be utilized in emergency situations to bond soft biological tissue.

EXAMPLES

Figure 5:
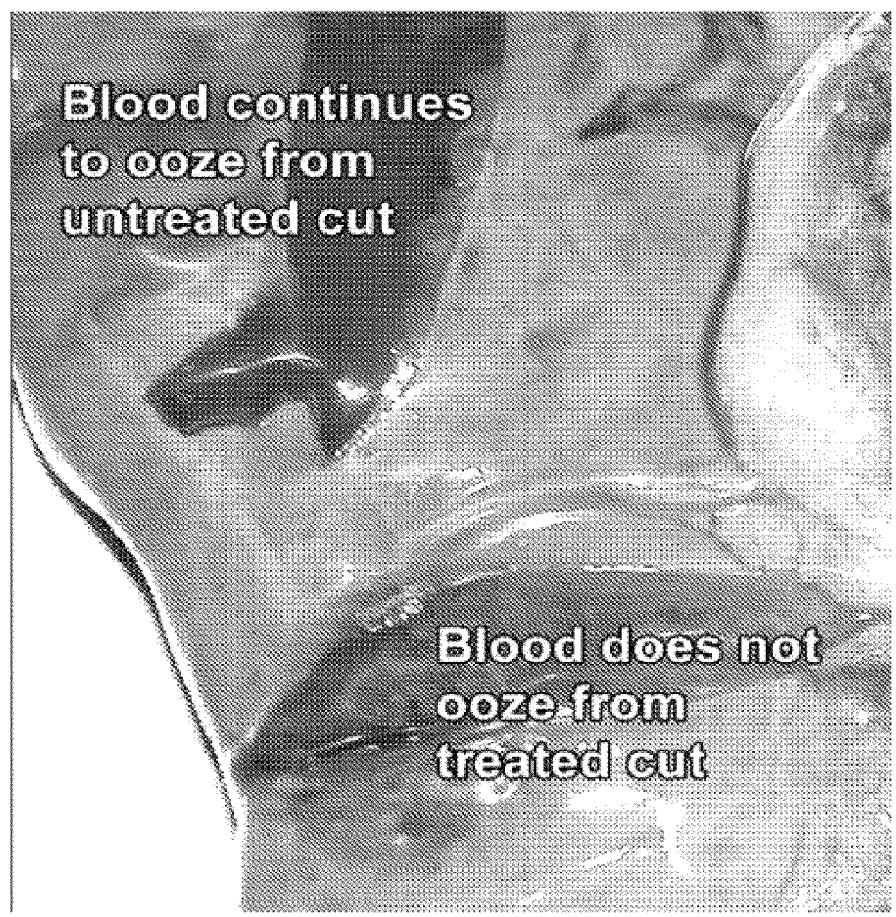
FIG. 5 shows a control tissue sample and a tissue sample that had been treated with non-thermal plasma.

Using non-thermal plasma device 100, blood coagulation tests have been performed on blood and blood from cow liver. The tests showed faster coagulation of the blood when exposed to the non-thermal plasma, as compared to coagulation without additional treatment. In one test, as seen in FIG. 5, a cow liver was cut in two places. The cut treated with non-thermal plasma coagulated. Additionally, no tissue damage was observed and the wound remained wet.

Figure 6:
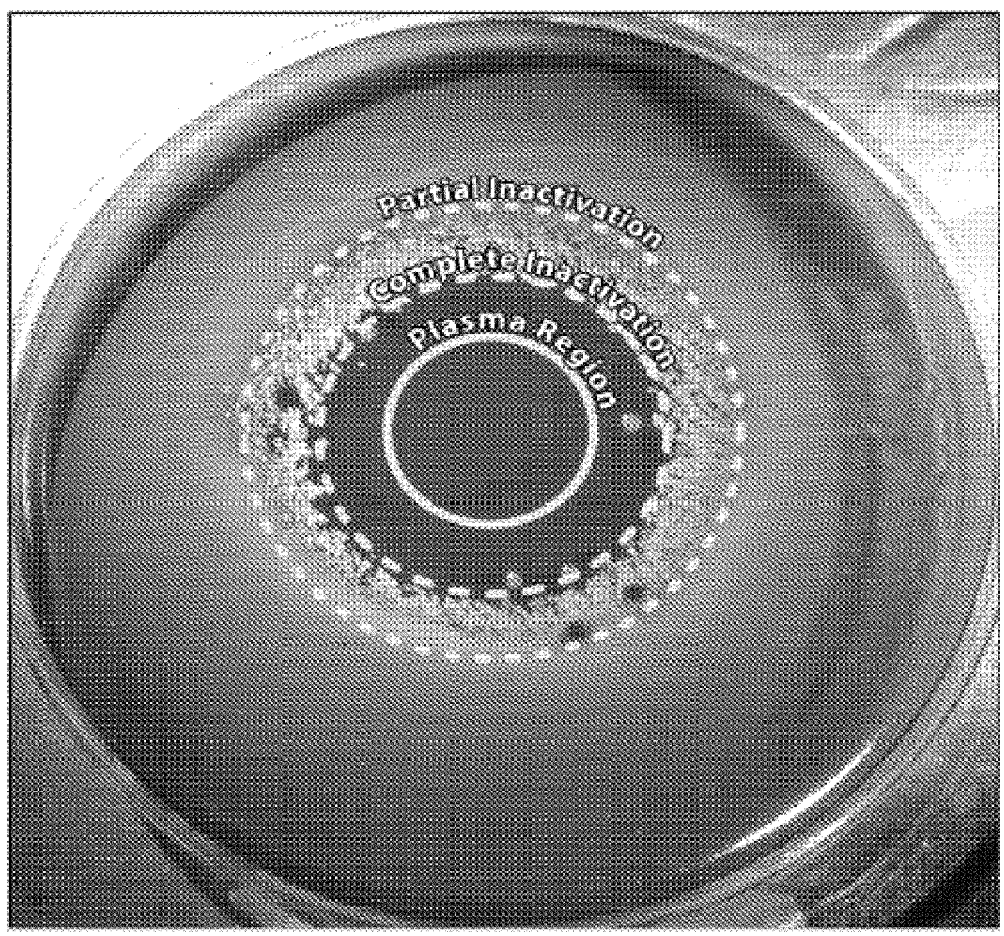
FIG. 6 shows decontamination categorization on a blood agar contaminated with ca. $10^7$ CFU/ml of skin flora that has been treated with non-thermal plasma.
Figure 7A:
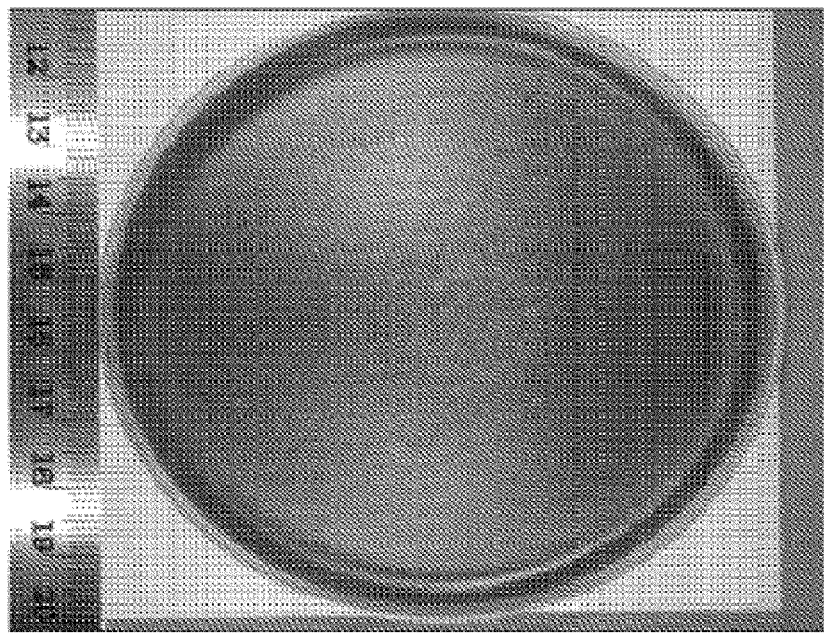
FIG. 7a shows blood agar treated with an embodiment of the present invention characterized as being a small non-thermal plasma jet emanating from a dielectric conduit having a diameter of 6 mm. The blood agar was treated for a period of 15 seconds.
Figure 7B:
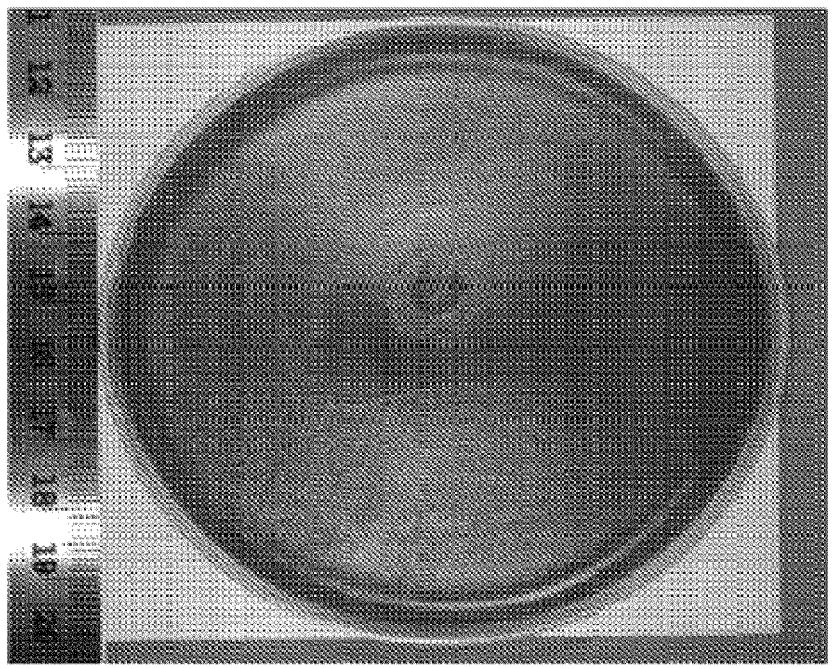
FIG. 7b shows blood agar treated with an embodiment of the present invention characterized as being a big non-thermal plasma jet emanating from a dielectric conduit having a diameter of 1 cm. The blood agar was treated for a period of 60 seconds.

Decontamination studies were also performed on blood agar contaminated with ca. $10^7$ CFU/ml of skin flora (*Streptococcus, Staphylococcus*, Yeast). FIG. 6 shows a decontamination categorization, showing a plasma region, complete inactivation, and partial inactivation. The plasma region is the point where the non-thermal plasma contacts the blood agar. The complete inactivation area is the area that is completely sterilized without being directly contacted by the non-thermal plasma, whereas the partial inactivation area is where some sterilization, but not complete, occurred without being directly contacted by the non-thermal plasma. FIG. 7a shows blood agar treated with a small jet, from a dielectric conduit 102 with a diameter of 6 mm, for a period of 15 seconds. FIG. 7b shows blood agar treated with a big jet, from a dielectric conduit 102 with a diameter of 1 cm, for a period of 60 seconds. The results showed that remote/weakly transferring jets were slower at decontaminating the surface. Additionally, direct jets could cause a 6 log reduction of an area larger than the dielectric conduit 102 diameter in less than 5 seconds.

While the embodiments have been described in connection with the preferred embodiments of the various features, it is to be understood that other similar embodiments may be used or modifications and additions may be made to the described embodiment for performing the same function without deviating therefrom. Therefore, the disclosed embodiments should not be limited to any single embodiment but rather should be construed in breadth and scope in accordance with the appended claims

What is claimed:

1. A method for contacting a biological substrate with non-thermal plasma, comprising:
    fluidicly communicating a gas through a dielectric conduit characterized as comprising an upstream end and a downstream end, the upstream end having an opening capable of receiving gas from a gas source, and the downstream end having an opening capable of transmitting non-thermal plasma therethrough;

energizing an RF electrode disposed circumferentially adjacent to an exterior wall of the dielectric conduit that in the presence of a floating igniter electrode disposed within an upstream portion of the dielectric conduit ionizes at least a portion of the gas to form a non-thermal plasma; and placing the biological substrate in a position no further than a first distance from the downstream opening of the dielectric conduit, wherein the first distance is a distance where discharge of the non-thermal plasma is characterized as being in a transferring mode, in which the non-thermal plasma first impinges on a surface of the biological substrate in a cloud shape, such that the substrate acts as ground.

2. The method of claim 1, further comprising:

providing the gas, from the gas source, to the upstream end of the dielectric conduit; and supplying RF power to the RF electrode via a power supply.

3. The method of claim 2, wherein the gas comprises helium, argon, nitrogen, air, or any combination thereof.

4. The method of claim 1, wherein the biological substrate comprises soft tissue, biological tissue, metal, plastic, or a combination thereof.

5. The method of claim 1, wherein the biological substrate is treated in a manner that effects at least some sterilization of the contacted area.

6. The method of claim 1, wherein the biological substrate is treated in a manner that promotes the coagulation of blood, thermal coagulative bonding, or chemical denaturing bonding.

7. The method of claim 1, wherein the biological substrate is exposed to the non-thermal plasma discharge for a duration in the range of about 3 seconds to about 2 minutes.

8. The method of claim 1, comprising:

placing the biological substrate at a second distance from the downstream opening of the dielectric conduit, wherein the second distance is closer to the downstream opening of the dielectric conduit than is the first distance; and wherein the second distance is a distance where discharge of the non-thermal plasma is characterized as being in an attached mode with respect to the biological substrate, in which the non-thermal plasma discharge impinges the surface of the biological substrate in a focused, intense microcolumn.

9. The method of claim 1, wherein the dielectric conduit comprises glass, quartz, plastic, ceramic, porcelain, or a combination thereof.

10. The method of claim 1, wherein the dielectric conduit has a diameter in the range of about 0.2 mm and about 1 cm.

11. The method of claim 1, wherein the RF electrode comprises water, aluminum foil, stainless steel, stainless steel mesh, copper, silver, any other conducting material, or any combination thereof.

12. The method of claim 1, wherein the RF electrode has a length in the range of about 1 mm to about 20 cm.

13. The method of claim 1, wherein the igniter electrode comprises tungsten, copper, gold, silver, iron, titanium, platinum, aluminum, any other metal, or any combination thereof.

14. The method of claim 1, wherein the igniter electrode comprises a wire.

15. The method of claim 1, wherein the igniter electrode is located proximate to the center of the lumen of the dielectric conduit.

16. The method of claim 1, wherein the igniter electrode is positioned upstream of the RF electrode.

17. The method of claim 1, wherein at least a portion of the igniter electrode overlaps the RF electrode.

18. The method of claim 1, wherein the dielectric conduit is a tube, cylindrical tube, rectangular prism, or pyramid.

* * * * *